United States Patent [19]

Tarabishy

[11] Patent Number: 5,702,398
[45] Date of Patent: Dec. 30, 1997

[54] TENSION SCREW

[76] Inventor: Sam Tarabishy, 11339 Cortez Blvd., Suite 106, Brooksville, Fla. 34613-5404

[21] Appl. No.: 803,574

[22] Filed: Feb. 21, 1997

[51] Int. Cl.[6] .................................................. A61B 17/00
[52] U.S. Cl. ............................ 606/72; 606/104; 606/232; 623/13
[58] Field of Search .......................... 606/72–75, 104, 606/232; 623/13

[56] References Cited

U.S. PATENT DOCUMENTS

| | | | |
|---|---|---|---|
| 2,121,193 | 12/1938 | Hanicke | 606/104 |
| 4,484,570 | 11/1984 | Sutter et al. | 606/72 |
| 4,590,928 | 5/1986 | Hunt et al. | 128/92 D |
| 4,778,468 | 10/1988 | Hunt et al. | 623/16 |
| 5,108,433 | 4/1992 | May et al. | 623/13 |
| 5,139,520 | 8/1992 | Rosenberg | 623/13 |
| 5,152,790 | 10/1992 | Rosenberg et al. | 623/13 |
| 5,207,679 | 5/1993 | Li | 606/72 |
| 5,217,486 | 6/1993 | Rice et al. | 606/232 |
| 5,370,646 | 12/1994 | Reese et al. | 606/104 |
| 5,376,119 | 12/1994 | Zimmermann et al. | 673/13 |
| 5,458,601 | 10/1995 | Young, Jr. et al. | 606/72 |

*Primary Examiner*—Gary Jackson
*Attorney, Agent, or Firm*—David W. Pettis, Jr., PA

[57] ABSTRACT

A tension screw of the type primarily intended for anchoring one end of a ligament graft to a bone during surgery to repair a damaged or torn ligament. The tension screw includes two principal elements: a cannulated screw and a bone screw which is insertable through the longitudinal bore of the cannulated screw. The bone screw actually anchors the graft to a bone, while the cannulated screw includes a small hook for attaching the ligament graft thereto. The cannulated screw is free to rotate around the bone screw so as to place the ligament graft under tension. Then, the bone screw is tightened into the bone, fixing the graft to the bone.

11 Claims, 4 Drawing Sheets

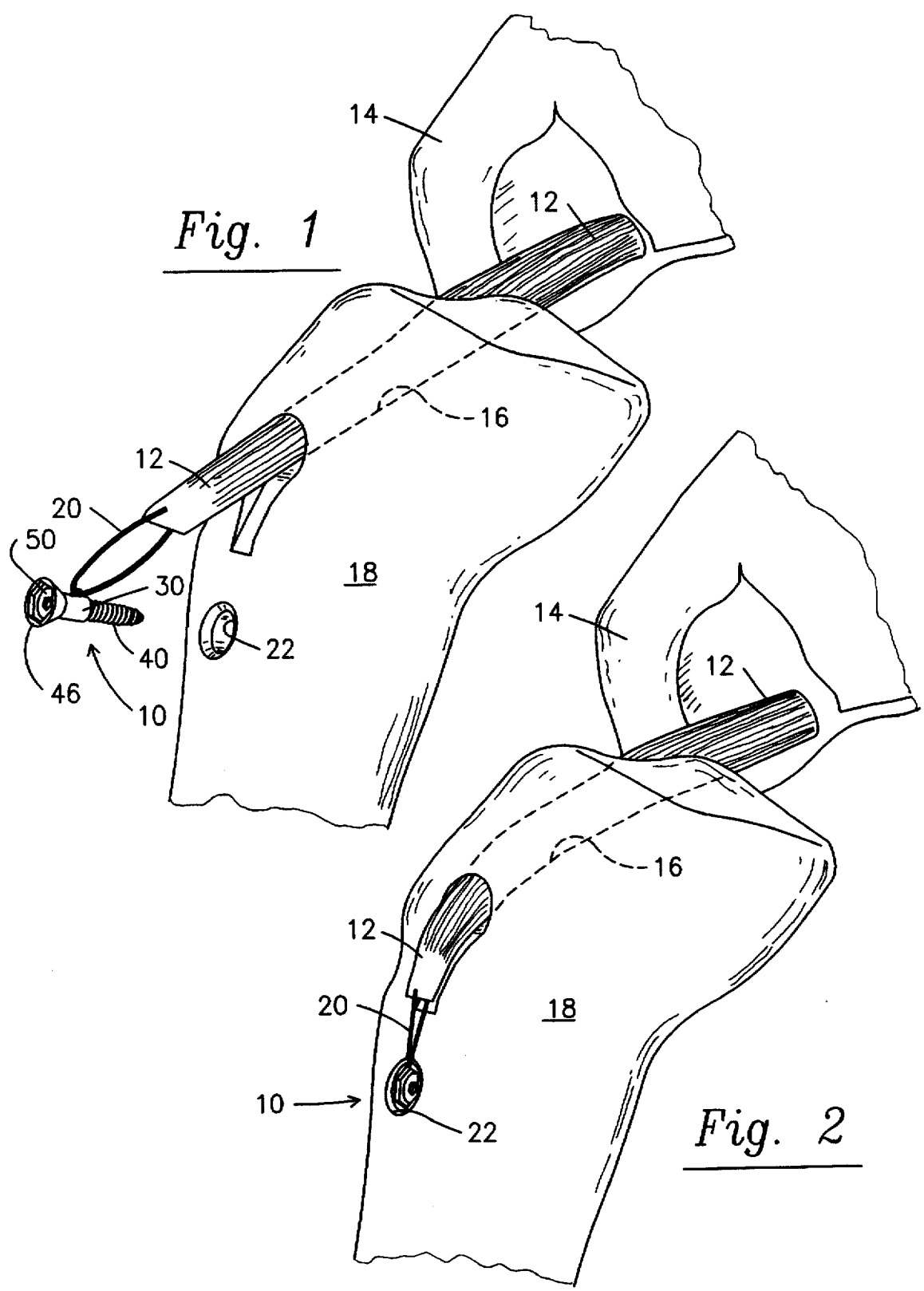

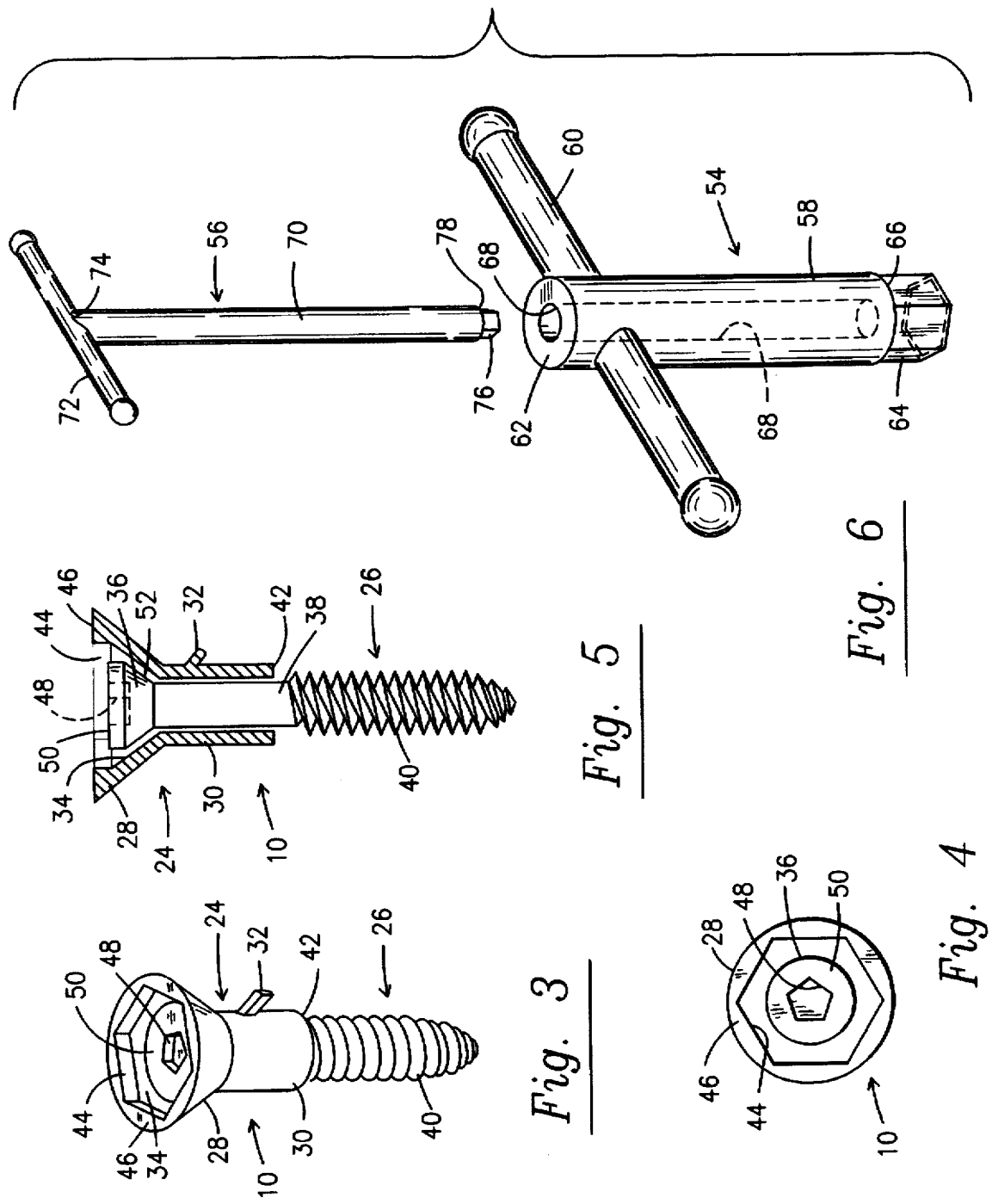

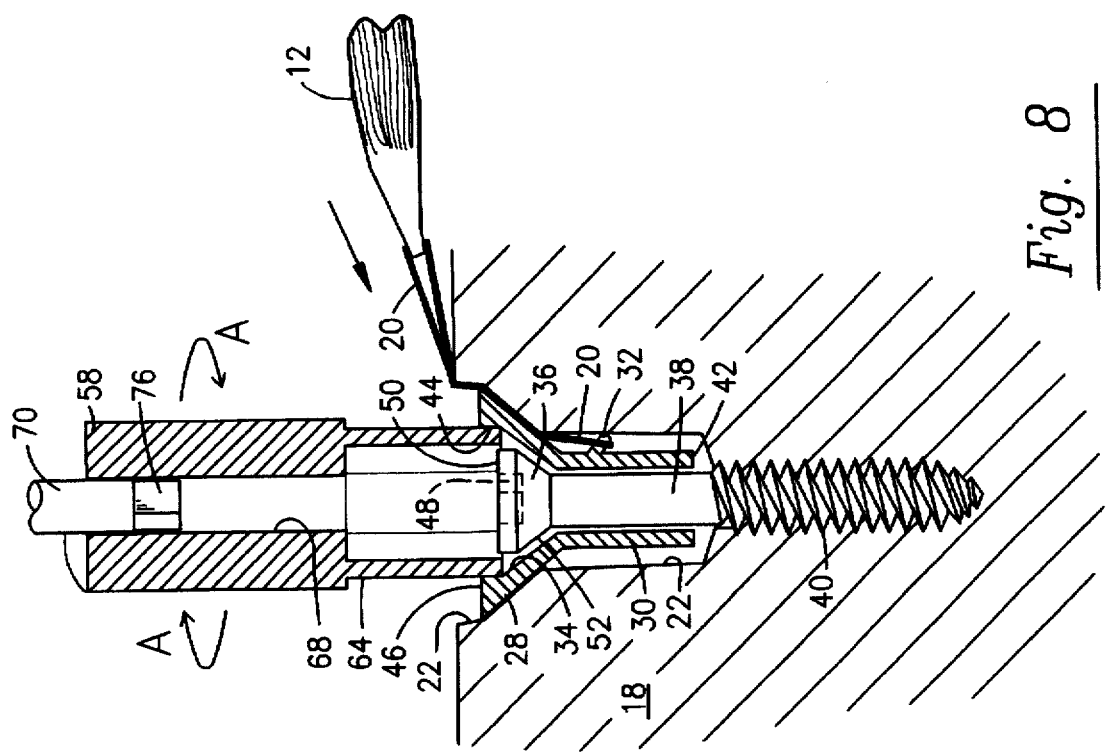
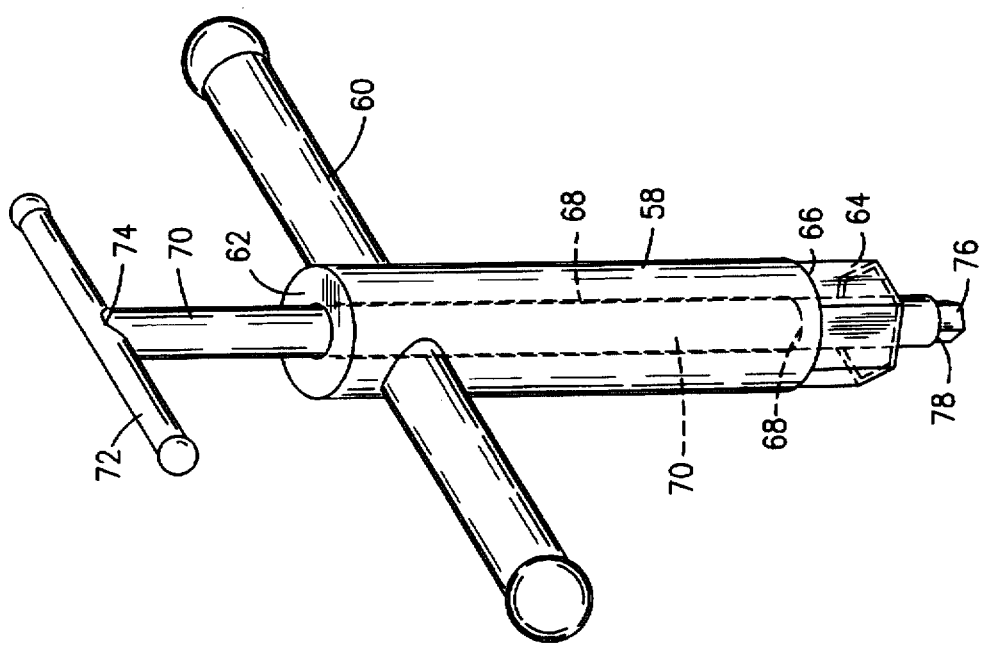

TENSION SCREW

BACKGROUND OF THE INVENTION

1. Field of the Invention

The present invention relates to a tension screw primarily intended for anchoring one end of a ligament graft to a bone during surgery to repair a damaged or torn ligament. The tension screw of this invention is uniquely characterized by its construction comprising a cannulated screw and a bone screw that is insertable through the longitudinal bore of the cannulated screw. The cannulated screw is free to rotate about the bone screw, and the cannulated screw includes a small hook, or projection, extending radially from its shaft for attachment of the ligament graft thereto. Rotation of the cannulated screw applies tension to the ligament graft, and full insertion of the bone screw locks the cannulated screw into position, completing attachment of the graft.

2. Description of the Prior Art

There are a large number of anterior cruciate ligament reconstruction surgeries performed annually in the United States and around the world. This surgery, in principle, involves taking a tendon graft from around the knee and using it as an anterior cruciate ligament that the patient has lost. The surgeon harvests the graft, and that graft is shaped to the size and dimension of the damaged ligament. The graft is then passed through two tunnels or passageways: one in the patient's femur, and one in the patient's tibia. The graft is positioned in the middle of the knee where the damaged cruciate ligament normally exists. Fixation of the ends of the graft to the bone so as to provide good tension is quite important to the success of such reconstructive surgery. Numerous devices have been proposed to stabilize the ends of the graft to the bone, such as, for example, screws, metal staples, and a variety of buttons. One problem inherent with virtually all such prior art devices is the fact that while the surgeon is placing the graft, after anchoring the first end of the graft, the surgeon must maintain tension on the graft while anchoring the free end. That tension is generally applied manually and, after the free end of the graft is attached, the surgeon then tests the knee for stability to determine if the tension on the graft is appropriate for that patient. Obviously, then, if the tension is too little or too great, one end of the graft must be released from the bone and further attempts at fixation with proper tension are then made by the surgeon.

In recognition of the inherent problem of properly tensioning a ligament graft, prior patent literature discloses and teaches a number of proposed solutions. For example, U.S. Pat. No. 5,458,601 to Young, et al., discloses an adjustable ligament anchor for attaching a ligament to a bone. According to the teaching of that patent, a housing having a longitudinal bore therethrough is fixed to a bone of the patient. Insertable into the housing is a member to which one end of the ligament graft can be attached. This member is dimensioned and configured to move within the housing along its longitudinal dimension, and includes a threaded internal passageway formed therein. The third element of this device is a threaded screw which engages the member to which the ligament graft is attached. The threaded screw engages the internal threads of the member such that turning the screw will cause the member to move within the housing. Thus, turning the screw will either loosen or tighten tension on the ligament attached to the member.

U.S. Pat. No. 5,376,199 to Zimmermann, et al., discloses another apparatus for anchoring a ligament graft wherein a housing is fixed to the patient's bone, that housing including a threaded, longitudinal bore which intersects with a transverse bore. One end of the ligament graft is extended through the transverse bore of the housing, and a device in the nature of a set screw is inserted into the threaded bore so that the distal end of the set screw physically engages and holds the end of the tendon graft.

Another anchoring apparatus is taught in U.S. Pat. No. 5,152,790 to Rosenberg, et al. The apparatus of that patent basically provides for adjusting tension on the ligament graft by adjusting the position of its anchor assembly along the longitudinal dimension of a tunnel formed in the patient's femur to which the graft is attached.

U.S. Pat. No. 5,108,433 to May, et al., discloses a turnbuckle-type attachment for tensioning a ligament graft.

Other exemplar prior art devices are disclosed in U.S. Pat. Nos. 4,590,928; 4,778,468; 5,139,520; 5,207,679; and 5,217,486.

While virtually all of the prior art devices identified above are useful for attaching ligament grafts during reconstructive surgery, and are constructed to permit adjustments to the tension placed on the ligament graft, the disclosed devices are relatively complex in their construction, and many, if not most, call for relatively large passageways or tunnels to be formed in the bone to which the adjustable fixation is made. It is, therefore, clear that there remains a great need in the art of ligament reconstructive surgery for a device which permits attachment of ligament grafts in a simple, relatively non-invasive manner, while providing for ease in adjusting the tension applied to the graft. Obviously, such a device must be suitable for implantation into the human body, should cause as little trauma as possible, and should permit case of access for adjusting tension even weeks, months, or years after the original surgery.

SUMMARY OF THE INVENTION

The present invention relates to a tension screw of the type primarily intended for anchoring one end of a ligament graft to a bone during surgery to repair a ligament such as, for example, repair of a torn anterior cruciate ligament. The tension screw of this invention comprises a cannulated screw having a head and a shaft extending distally from the head. A hook-type projection extends radially from a segment of the shaft such that an end of the ligament graft may be attached to the projection. The tension screw further comprises a bone screw dimensioned and configured to extend through the longitudinal bore of the cannulated screw, and the bone screw comprises a bone screw head, a body extending distally from the bone screw head, and a threaded shaft extending distally from the body. When inserted into and through the cannulated screw, the threaded shaft of the bone screw extends longitudinally beyond a distal end of the cannulated screw shaft, whereby the bone screw may be attached to the bone.

In a preferred embodiment, the tension screw further comprises a first toughened surface formed on an interior portion of the cannulated screw head, and a second toughened surface formed on a distal portion of the bone screw head in engaging relation to the first roughened surface when the bone screw is fully tightened into the bone.

The cannulated screw is rotatable around the bone screw until the bone screw has been fully tightened into the bone so that rotation of the cannulated screw will result in increasing or decreasing (dependent upon the direction of rotation) the tension applied to the ligament graft which is attached to the hook extending from the cannulated screw shaft.

3

In the preferred embodiment, the cannulated screw head is dimensioned and configured to receive an implement whereby the cannulated screw head may be rotated. The bone screw head further comprises a tool receptor formed in a proximal surface of the bone screw head whereby a tool may be operatively engaged with the receptor to attach the bone screw to the bone and to tighten the bone screw fully into the bone.

The invention accordingly comprises an article of manufacture possessing the features, properties, and the relation of elements which will be exemplified in the article hereinafter described, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which:

FIG. 1 is an illustration of the tension screw of this invention positioned for attaching a ligament graft.

FIG. 2 is a view similar to that of FIG. 1 showing the ligament graft attached by the tension screw.

FIG. 3 illustrates a preferred embodiment for the tension screw of this invention.

FIG. 4 is a top, plan view of the tension screw of FIG. 3.

FIG. 5 is a side elevation, partially in section, of the tension screw of FIG. 3

FIG. 6 is an exploded view of the insertion tool used to position the tension screw of FIG. 3.

FIG. 7 is a perspective view of the insertion tool of FIG. 6 with interior detail shown in broken lines.

FIG. 8 is a side elevation, partially in section, showing use of the insertion tool of FIG. 6, in combination with the tension screw of FIG. 3, to tension the ligament graft.

DETAILED DESCRIPTION

Figure 9:
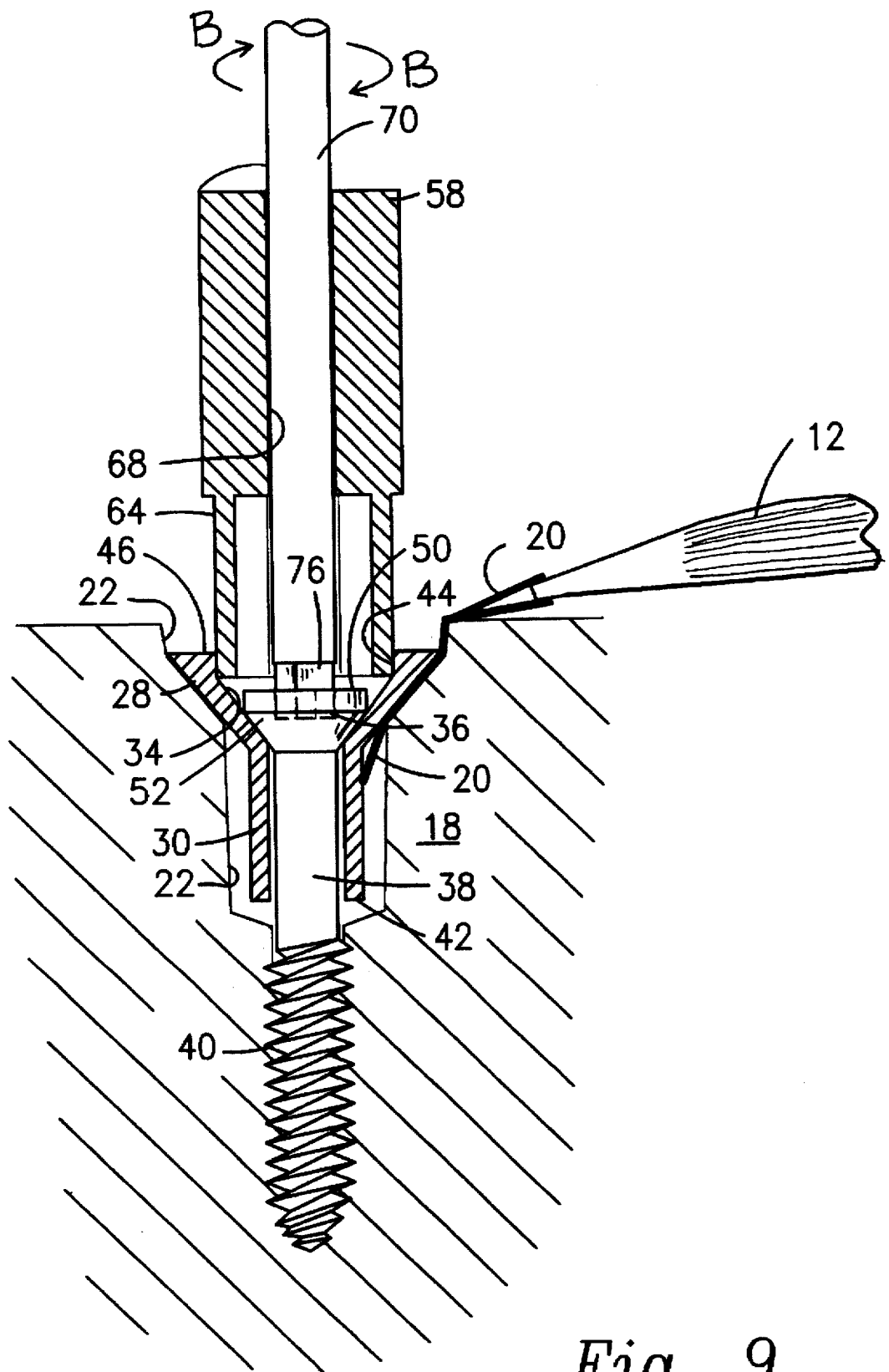
FIG. 9 is a view similar to that of FIG. 8, showing use of the insertion tool to fix the position of the tension screw of FIG. 3, as shown in the view of FIG. 2. Similar reference characters refer to similar parts throughout the several views of the drawings.

Throughout the drawing figures, the tension screw of this invention is generally indicated as 10. Referring first to the views of FIGS. 1 and 2, and with regard to anterior cruciate ligament reconstructive surgery, for example, the surgeon first prepares a ligament graft 12 and attaches one end (not shown) of graft 12 to the patient's femur 14. Having drilled a graft passageway 16 through the patient's tibia 18, the surgeon extends graft 12 through passageway 16 for attachment to tibia 18. As shown in the views of FIGS. 1 and 2, attachment of graft 12 to tibia 18 is typically accomplished by means of a suture 20. Attachment and tensioning of the graft 12 to tibia 18 is accomplished by inserting tension screw 10 into screw socket 22, that socket 22 having been drilled into tibia 18 during the course of the reconstructive surgery.

Attention is now invited to the views of FIGS. 3, 4 and 5 for a description of a preferred embodiment of tension screw 10. As perhaps best seen in the view of FIG. 5, tension screw 10 comprises a cannulated screw generally indicated as 24 and a bone screw generally indicated as 26. Cannulated screw 24 is shown in section in the view of FIG. 5.

Cannulated screw 24 comprises a head 28 and a shaft 30 extending distally from head 28. A hook-type projection 32

4 extends radially from a segment of shaft 30. Finally, a first roughened surface 34 may be provided on the interior portion of cannulated screw head 28.

Bone screw 26 is dimensioned and configured to extend through cannulated screw 24 and comprises a bone screw head 36, a body 38 extending distally from bone screw head 36, and a threaded shaft 40 extending distally from body 38. As clearly seen in the views of FIGS. 3 and 5, threaded shaft 40 extends longitudinally beyond distal end 42 of shaft 30.

While clearly shown in each of the views of FIGS. 3, 4, and 5, the view of FIG. 4 clearly illustrates that, in this preferred embodiment, a hexagonal recess 44 is formed at the proximal end 46 of cannulated screw head 28. A pentagonal recess 48 is formed in the proximal surface 50 of bone screw head 36. The purpose of recesses 44 and 48 is described in greater detail hereinafter. Finally, a second roughened surface 52 may be provided on a distal portion of bone screw head 36 in engaging relation to first roughened surface 34 when bone screw 26 is fully tightened into the tibia 18, as shown in the view of FIG. 9.

Tension screw 10 further comprises an implement, generally indicated as 54, used for tensioning ligament graft 12, and a tool, generally indicated as 56, used for attaching tension screw 10 into the tibia 18. Referring to the exploded view of FIG. 6, implement 54 comprises an elongated implement body 58, a handle 60 formed at proximal end 62 of implement body 58, and a driver 64 formed at distal end 66 of implement body 58. A longitudinal bore 68 is formed through implement body 58 so that tool 56 may be inserted therein.

Still referring to the exploded view of FIG. 6, it can be seen that tool 56 comprises an elongated tool body 70, a tool handle 72 formed at proximal end 74 of tool body 70, and a driving tip 76 formed at distal end 78 of tool body 70.

As clearly seen in the views of FIGS. 7, 8 and 9, tool handle 72 is dimensioned and configured so as to pass freely through longitudinal bore 68 such that handle 60 may be used to rotate implement 54, as indicated by directional arrows A in the view of FIG. 8, independently from tool 56. In like fashion, tool handle 72 may be used to rotate tool 56 independently of implement 54, as shown by directional arrows B.

In order to use the tension screw 10 of this invention for applying tension to ligament graft 12 and fixing the graft 12 in place to tibia 18, the patient is prepared as shown in the view of FIG. 1. Suture 20 is engaged onto projection 32, and the assembled implement 54 and tool 56 combination are then used to insert bone screw 26 through screw socket 22 and into the patient's tibia 18. Then, tool 56 is retracted, basically as shown in the view of FIG. 8, and driver 64 is engaged with hexagonal recess 44 and handle 60 is used by the surgeon to apply tension to ligament graft 12. When properly tensioned, to the satisfaction of the surgeon, tool 56 is advanced through longitudinal bore 68 such that driving tip 76 engages pentagonal recess 48. Handle 72 is then turned to seat bone screw 26 fully into tibia 18, resulting in frictional engagement between first roughened surface 34 and second roughened surface 52 to accomplish final fixation of the graft 12. After appropriate testing by the surgeon, and readjustment of the tension on graft 12 if necessary, the incision is closed and the surgery is completed.

Should it become necessary to readjust the tension placed on graft 12 at some point in the future, even after the surgery has completely healed, such adjustment can be accomplished, in most instances, under local anesthesia. A small incision to permit access to tension screw 10 by the surgeon utilizing implement 54 and 56 would readily permit such adjustments.

It will thus be seen that the objects set forth above, among those made apparent from the preceding description, are efficiently attained, and, since certain changes may be made in the above article without departing from the scope of the invention, it is intended that all matter contained in the above description or shown in the accompanying drawings shall be interpreted as illustrative and not in a limiting sense.

It is also to be understood that the following claims are intended to cover all of the genetic and specific features of the invention herein described, and all statements of the scope of the invention which, as a matter of language, might be said to fall therebetween.

Now that the invention has been described,
What is claimed is:

1. A tension screw of the type primarily intended for anchoring one end of a ligament graft to a bone during surgery to repair a ligament, said tension screw comprising: a cannulated screw having a head and a shaft extending distally from said head, said cannulated screw further comprising a hook-type projection extending radially from a segment of said shaft, whereby an end of the ligament graft may be attached to said projection; and a bone screw dimensioned and configured to extend through said cannulated screw, said bone screw comprising a bone screw head, a body extending distally from said bone screw head, and a threaded shaft extending distally from said body, said threaded shaft extending longitudinally beyond a distal end of said cannulated screw shaft, whereby said bone screw may be attached to the bone.

2. A tension screw as in claim 1 wherein said tension screw further comprises a first roughened surface formed on an interior portion of said cannulated screw head in engaging relation to said bone screw head when said bone screw is fully tightened into the bone.

3. A tension screw as in claim 1 wherein said bone screw further comprises a second roughened surface formed on a distal portion of said bone screw head in engaging relation to said cannulated screw head when said bone screw is fully tightened into the bone.

4. A tension screw as in claim 1 wherein said cannulated screw is rotatable around said bone screw until said bone screw is fully tightened into the bone.

5. A tension screw as in claim 1 wherein said cannulated screw head is dimensioned and configured to receive an implement whereby said cannulated screw may be rotated around said bone screw to apply tension to the ligament graft attached to said projection.

6. A tension screw as in claim 5 wherein said bone screw head further comprises a tool receptor formed in a proximal surface thereof whereby a tool may be operatively engaged with said receptor to attach said bone screw to the bone and to tighten said bone screw fully into the bone.

7. A tension screw as in claim 6 further comprising means for tensioning the ligament graft attached to said projection, said means for tensioning comprising an implement comprising an elongated implement body, a handle formed at a proximal end of said implement body, a driver formed at a distal end of said implement body, said driver being dimensioned and configured to be received by said cannulated screw head, and a longitudinal bore formed through said implement body.

8. A tension screw as in claim 7 further comprising means for attaching said bone screw into the bone, said means for attaching comprising a tool comprising an elongated tool body, a handle formed at a proximal end of said tool body, a driving tip formed at a distal end of said tool body, said driving tip being dimensioned and configured to be received by said tool receptor, said tool body having an exterior surface dimensioned and configured to be received by said longitudinal bore and being free to rotate about its longitudinal axis within said bore.

9. A tension screw of the type primarily intended for anchoring one end of a ligament graft to a bone during surgery to repair a ligament, said tension screw comprising:
a cannulated screw having a head and a shaft extending distally from said head, said cannulated screw further comprising
a hook-type projection extending radially from a segment of said shaft, whereby an end of the ligament graft may be attached to said projection, and
a first roughened surface formed on an interior portion of said cannulated screw head in engaging relation to said bone screw head when said bone screw is fully tightened into the bone; and
a bone screw dimensioned and configured to extend through said cannulated screw, said bone screw comprising
a bone screw head, a body extending distally from said bone screw head, and a threaded shaft extending distally from said body, said threaded shaft extending longitudinally beyond a distal end of said cannulated screw shaft, whereby said bone screw may be attached to the bone;
said bone screw further comprising a second toughened surface formed on a distal portion of said bone screw head in engaging relation to said first roughened surface when said bone screw is fully tightened into the bone;
said cannulated screw being rotatable around said bone screw until said bone screw is fully tightened into the bone.

10. A tension screw as in claim 9 wherein said cannulated screw head is dimensioned and configured to receive an implement whereby said cannulated screw may be rotated around said bone screw to apply tension to the ligament graft attached to said projection, and wherein said bone screw head further comprises a tool receptor formed in a proximal surface thereof whereby a tool may be operatively engaged with said receptor to attach said bone screw to the bone and to tighten said bone screw fully into the bone.

11. A tension screw as in claim 10 further comprising means for tensioning the ligament graft attached to said projection and means for attaching said bone screw into the bone,
said means for tensioning comprising an implement comprising an elongated implement body, a handle formed at a proximal end of said implement body, a driver formed at a distal end of said implement body, said driver being dimensioned and configured to be received by said cannulated screw head, and a longitudinal bore formed through said implement body; and
said means for attaching comprising a tool comprising an elongated tool body, a handle formed at a proximal end of said tool body, a driving tip formed at a distal end of said tool body, said driving tip being dimensioned and configured to be received by said tool receptor, said tool body having an exterior surface dimensioned and configured to be received by said longitudinal bore and being free to rotate about its longitudinal axis within said bore.

* * * * *

UNITED STATES PATENT AND TRADEMARK OFFICE
CERTIFICATE OF CORRECTION

PATENT NO. : 5,702,398
DATED : December 30, 1997
INVENTOR(S) : Sam Tarabishy

It is certified that error appears in the above-indentified patent and that said Letters Patent is hereby corrected as shown below:

```
    Claim 9, column 6, line 29, delete "toughened"
and insert therefor --roughened--.
```

Signed and Sealed this

Tenth Day of March, 1998

Attest:

BRUCE LEHMAN

Attesting Officer        Commissioner of Patents and Trademarks